(12) United States Patent
Elkin et al.

(10) Patent No.: US 9,810,708 B2
(45) Date of Patent: Nov. 7, 2017

(54) AUTOMATED SAMPLING SYSTEM

(71) Applicants: The United States of America, as Represented by the Secretary of Agriculture, Washington, DC (US); The Penn State Research Foundation, University Park, PA (US)

(72) Inventors: Kyle R. Elkin, State College, PA (US); Randall G. Bock, Phillipsburg, PA (US)

(73) Assignees: The United States of America, as represented by The Secretary of Agriculture, Washington, DC (US); The Penn State Research Foundation, University Park ( * ) Notice: Subject to any disclaimer, the term of this patent is extended or adjusted under 35 U.S.C. 154(b) by 0 days.

(21) Appl. No.: 14/933,383

(22) Filed: Nov. 5, 2015

(65) Prior Publication Data

US 2017/0131319 A1    May 11, 2017

(51) Int. Cl.
| | |
|---|---|
| *G01N 30/02* | (2006.01) |
| *G01N 30/96* | (2006.01) |
| *G01N 35/10* | (2006.01) |
| *B01D 15/12* | (2006.01) |
| *G01N 1/40* | (2006.01) |
| *G01N 35/00* | (2006.01) |
| *G01N 30/00* | (2006.01) |

(52) U.S. Cl.
CPC ....... *G01N 35/1097* (2013.01); *B01D 15/125* (2013.01); *G01N 1/4044* (2013.01); *G01N 1/4077* (2013.01); *G01N 30/96* (2013.01); *G01N 35/00871* (2013.01); *G01N 2001/4088* (2013.01); *G01N 2030/0095* (2013.01); *G01N 2035/00475* (2013.01)

(58) Field of Classification Search
CPC ............................................. G01N 2030/0095
See application file for complete search history.

(56) References Cited

U.S. PATENT DOCUMENTS

2007/0277596 A1* 12/2007 Kim ..................... G01N 21/645
                                                              73/61.48
2008/0116908 A1* 5/2008 Potyrailo ............. G21C 17/022
                                                              324/721

* cited by examiner

*Primary Examiner* — Paul Hyun
(74) *Attorney, Agent, or Firm* — John D. Fado; Robert D. Jones

(57) ABSTRACT

The automated sampling system has a water tight case that encloses a testing instrument. In the preferred embodiment, the testing instrument is a field-portable ion chromatography instrument designed to test water samples. In operation, a controller directs a syringe pump to draw fluid from outside the system through a specialized filter with a continuous flow lower reservoir. When directed by the controller, the syringe pump then injects the sample water into a testing portion of the field-portable ion chromatography instrument.

17 Claims, 4 Drawing Sheets

AUTOMATED SAMPLING SYSTEM

FIELD OF THE INVENTION

The disclosed method and apparatus relates to a system for automatically sampling a fluid wherein the sampling system is immersed or floating in the fluid targeted for sampling. Specifically, the system described herein relates to sampling system for a brief-case sized field-portable chromatography system instrument capable of continuously testing fluid samples in a body of fluid in which the instrument is disposed.

BACKGROUND OF THE INVENTION

The process of using a chromatography instrument to test fluid samples is a well-known means of monitoring fluid quality. However, the currently used processes are labor-intensive, expensive, and generally provide an uneven data stream. In accordance with the current most common process, a technician physically extracts a fluid sample and carries the sample back to a lab that is equipped with the required equipment.

However, using a technician to extract samples is slow and labor-intensive as well as expensive, and introduces an additional possibility of error. Even the best and most reliable technicians are not (at least theoretically) as dependable and consistent as a programmable machine. While at least one automated system for testing samples has been publicly disclosed, the inventor of the system disclosed herein has perfected a method and apparatus for automatically drawing a sample into a portable ion chromatography instrument and preparing the sample for testing.

SUMMARY OF THE INVENTION

This disclosure is directed to an auto-sampling system for a testing instrument, preferably a field-portable ion chromatography instrument. The instrument has a watertight outer shell. A control unit and all the hardware associated with the auto-sampling system is enclosed within the shell. The auto-sampling system comprises a syringe pump that is in hydraulic communication with the sample inlet filter and in electrical communication with the control unit. The inlet filter comprises a bottom unfiltered reservoir having an inlet and an outlet so that the bottom reservoir comprises a "continuous flow reservoir" (as defined in the body of this disclosure). The inlet filter has a substantially smaller top filtered reservoir, and a filter element positioned between the top and bottom reservoirs. A check valve is positioned between the inlet filter and the syringe pump.

In operation, the system is structured so that, during the auto-sampling process, when directed by the control unit, the plunger of the syringe pump is retracted so that suction force from the syringe pump causes fluid to move upward from the unfiltered bottom reservoir into the filtered top reservoir. The fluid then moves through the check valve, and into a sample loop of finite volume (as require for a specific application). When further directed by the control unit, the plunger is advanced so that the fluid is injected back through the check valve and into a testing portion of the field-portable ion chromatography instrument.

DETAILED DESCRIPTION OF PREFERRED EMBODIMENTS

Figure 1:
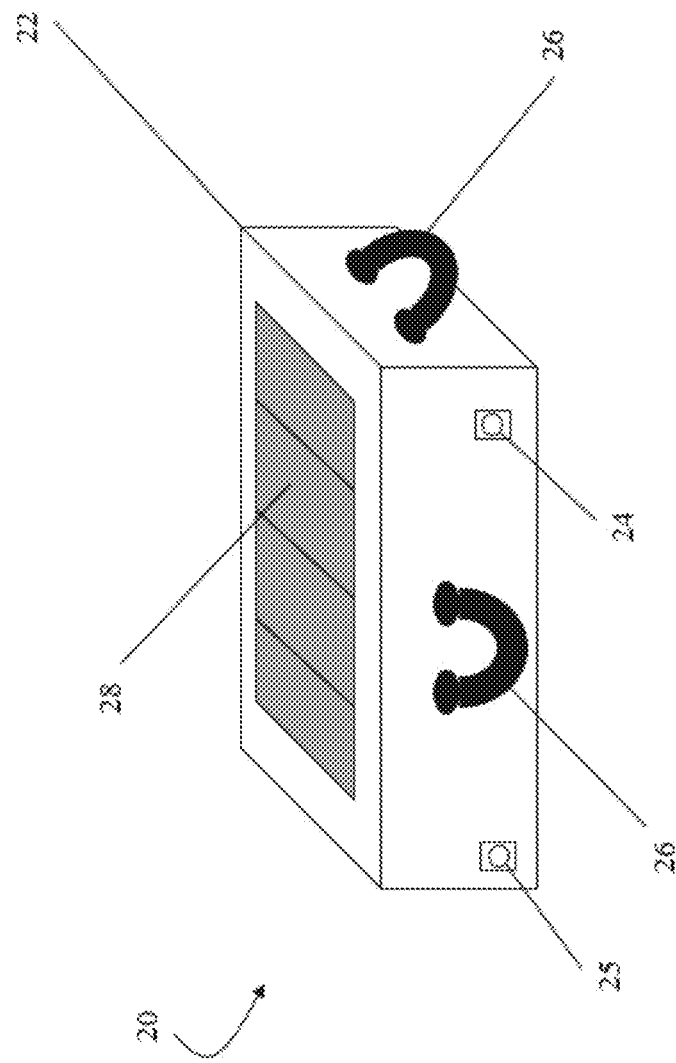
FIG. 1 is an elevational perspective view of the outer housing of the current system.

As generally shown in FIG. 1, the system described herein comprises an auto-sampling system for a field-portable and essentially self-contained chromatography instrument 20. In operation, the instrument 20 is designed to float in a body of fluid and continuously extract and test fluid samples. The data gathered by the system is wirelessly transmitted to a shore-based data processing unit.

As shown in FIG. 1, the instrument 20 comprises a rigid and fluid-tight outer shell 22. The shell 22 is designed to house all of the instrument components and subsystems. The only pathway for transport of fluid or gas through the instrument is through the fluid ports 24, 25. Aluminum frame mounts are used inside the shell 22 to provide a barrier, mounting surface, heat sink and faraday cage. When the instrument 20 is placed in a body of fluid, it can be tethered or anchored using at least one of a plurality of metal attachment brackets 26 that keep the instrument in position in the fluid.

In the preferred embodiment, the instrument outer shell 22 is generally rectangular with a length of about 22 inches, a width of 14 inches, and a vertical height of about 9 inches. In the preferred configuration, the instrument 20 weighs about 20 pounds. In alternative embodiments, the dimensions of the instrument 20 may be altered to accommodate the enclosed systems. Solar shielding 28 may be attached to the top of the outer shell 22 to aid with the passive cooling of the instrument 20. In the preferred embodiment, the solar shielding 28 comprises a solar panel and is used to power the instrument.

Figure 2:
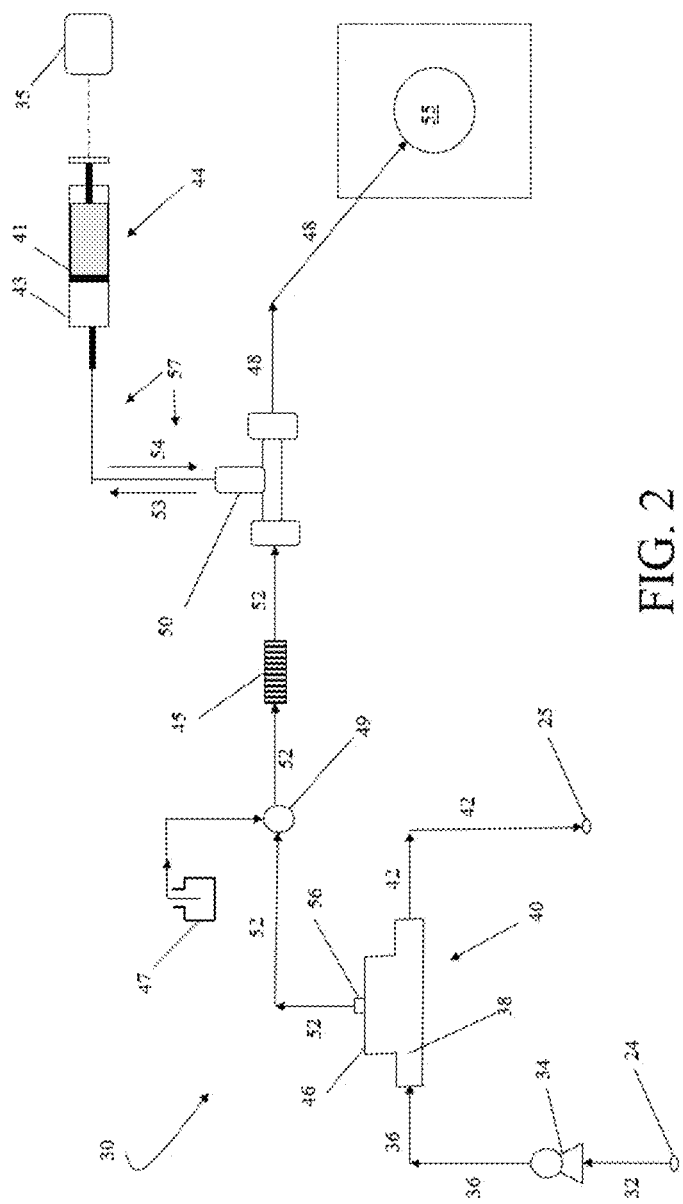
FIG. 2 is a schematic of the sampling system of the current instrument.

Prior to initiating the sampling process, fluid (preferably water) is drawn into the instrument 20 through a fluid port 24 in the in the instrument's outer shell 22 (per FIG. 1). FIG. 2 generally shows the sampling system 30 used to bring fluid into the instrument 20. As shown in FIG. 2, fluid is drawn into the instrument 20 through the fluid port 24 in the direction of the arrow 32 by the pump 34. Fluid is pumped in the direction of the arrow 36 and circulated through a bottom portion 38 of a filter 40, and then back out of the system in the direction of the arrow 42 through an exit port 25. Although the fluid ports 24, 25, are shown in FIG. 1 as positioned on the side of the shell 22, they may also be positioned on the top or bottom of the shell 22.

When the sampling process is initiated, a control unit 35 sends electronic instructions to a syringe pump 44. The control unit 35 may be pre-programmed to periodically draw samples, or may rely on sensors within the instrument 20 to initiate the sampling process. The control unit 35 may also be controlled through a wireless connection by a user or an electronic processor with the appropriate connection and communication equipment. A syringe pump 44 is used because of the pump's ability to repeatedly withdraw and dispense accurately the same volume of solution without cavitation. In other non-obvious embodiments, other types of pump may be utilized. When the plunger 41 of the syringe pump 44 is retracted, fluid is drawn out of the top portion 46 of the inlet filter 40 in the direction of the arrows 52 and 53.

The sample fluid then passes through a three-port valve 49, with one port of the three port valve being in fluid communication with a reagent reservoir 47. Based on the intended type of analyses of the fluid sample, the reagent stored in the reservoir 47 may be injected into the sample fluid. In the preferred embodiment, the reagent comprises a peroxysulfate salt (usually sodium or potassium). In alternative embodiments the reagent may be the salt or acid form of either peroxymonosulfate or peroxydisulfate.

The sample then proceeds to an inline digester 45, which comprises a heating element which heats the sample to approximately boiling temperature. The digester 45 promotes decomposition of the larger molecules into smaller components, which can be readily separated and quantified by the ion chromatograph. This process results in total nutrient value data, rather than a dissolved value. In the case of phosphorus, simply filtering the sample gives dissolved phosphorus data, whereas using the digester 45 will break up some organic molecules so that phosphorus is released resulting in a total phosphorus or total dissolved phosphorus value.

Fluid is then drawn through the check valve 50 and into the sample loop 57 in the direction of the arrow 53 by the syringe pump 44. The syringe pump 44 and sample loop 57 are initially filled with either air or a non-miscible fluid so that when the syringe plunger 41 is retracted, the incoming sample does not contaminate the syringe barrel 43.

Once the desired sample volume is obtained, the syringe plunger 41 is advanced so that the fluid in the sample loop 57 is injected in the direction of the arrow 54 back through the check valve 50 and into the testing portion of the instrument in the direction of the arrow 48. In the preferred embodiment, the sample fluid is directed toward a rotating injection valve 55 in a field-portable ion chromatography instrument 20.

Figure 3:
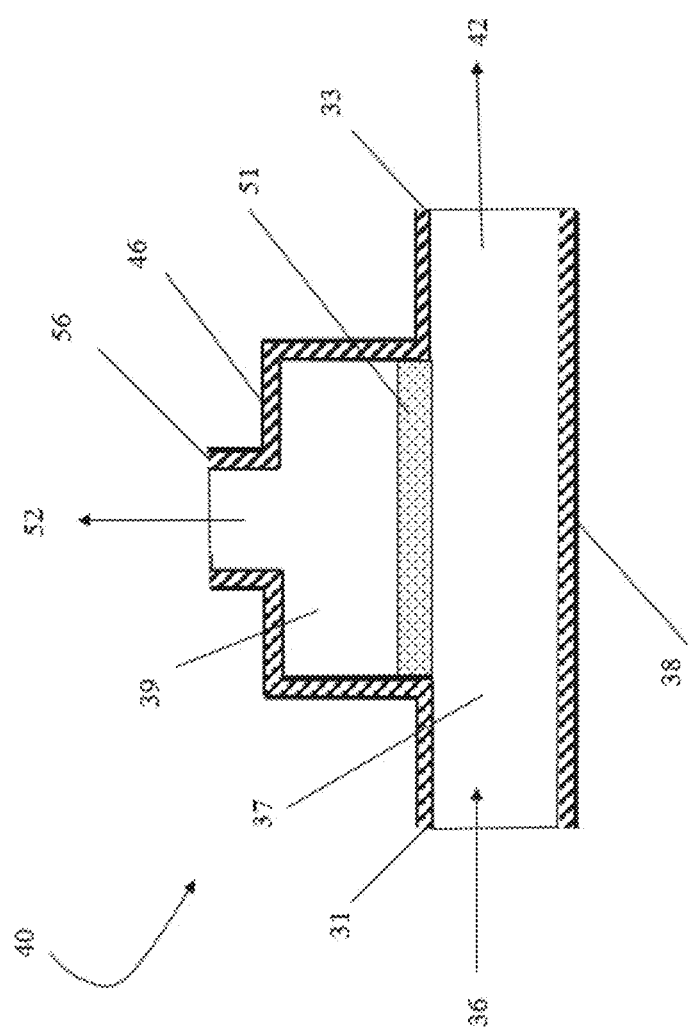
FIG. 3 is a sectional schematic view of the inlet filter for the current system.
Figure 4:
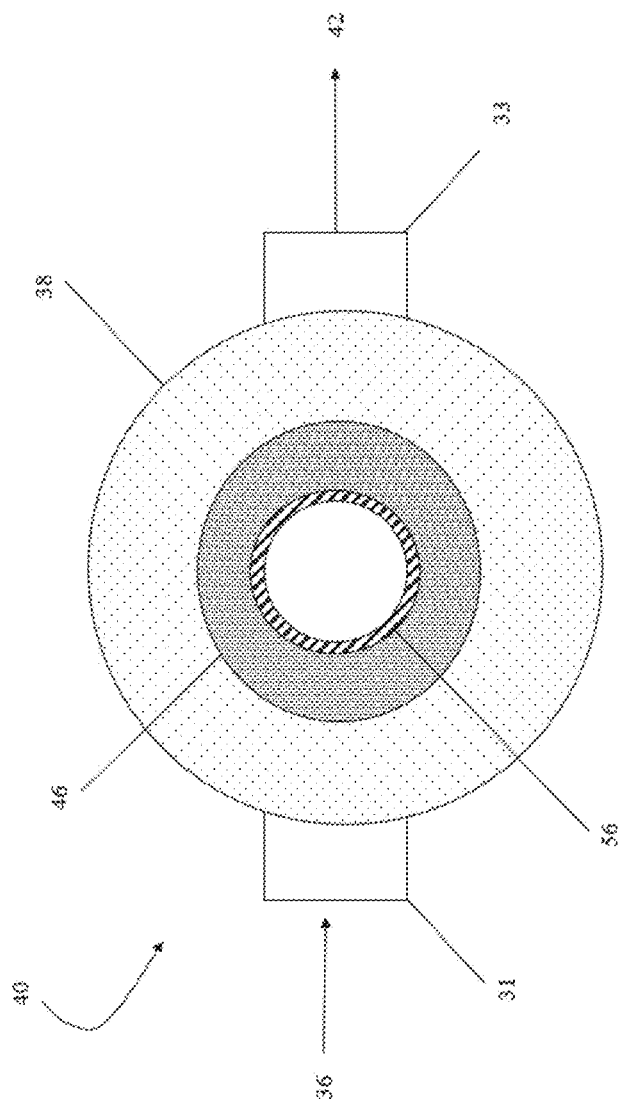
FIG. 4 is a top view of the inlet filter shown in FIG. 3.

FIGS. 3 and 4 show the filter 40 in greater detail. Prior to the sampling process, fluid is drawn through an inlet port 31 into a filter reservoir 37 in the bottom portion 38 of the filter inlet 40 (in the direction of the arrow 36). The "bottom reservoir" is more accurately described as the "unfiltered reservoir". The fluid in the bottom unfiltered reservoir 37 is then circulated out of a filter outlet port 33 in the direction of the arrow 42.

For the purposes of this application, a filter reservoir (as shown in FIG. 3) that permits fluid to essentially continuously flow into and out of the filter reservoir is defined as a "continuous flow filter reservoir". This configuration ensures minimal carry-over volume between samples—regardless of the distance between the sample intake port 24 and the inlet filter 40.

In the preferred embodiment, the bottom unfiltered filter reservoir 37 comprises a much larger reservoir (preferably 1-4 milliliters) than an upper filtered reservoir 39 (preferably 300-500 microliters) in the upper portion 46 of the inlet filter 40. In alternative embodiments, the respective volumes may be smaller than the 47 millimeter shown in the current embodiment. This design is used to minimize the chances that the inlet filter 40 will plug during sampling operations.

When the sampling process is initiated, fluid circulating through the unfiltered bottom portion 38 of the inlet filter 40 is drawn upwardly through a filter element 51 (shown in FIG. 3, but not FIG. 4) and into the upper filtered reservoir 30, then through the outlet port 56 in the direction of the arrow 52. In the preferred embodiment, the filter element 51 comprises a 0.45 micrometer nominal pore size, polyethersulfone membrane disk.

In operation, as fluid is circulated through a unfiltered bottom portion 38 of an inlet filter 40, a control unit 35 directs a syringe pump 44 to retract a syringe plunger 41 so that a fluid sample is drawn through an upper portion 46 of the filter 40 in the direction of the arrow 52. The fluid sample passes through a digester 45 and a check valve 50, and into a sample loop 57. Optionally, a reagent from the reservoir 47 may be added to the fluid sample as the sample passes through the valve 49. After the desired volume is attained, the syringe plunger 41 is advanced so that the fluid sample collected in the sample loop 57 is expelled and travels toward the check valve 50 in the direction of the arrow 54. The sample fluid flows then through the check valve 50 in the direction of the arrow 48, and then to a testing portion of an instrument. In the preferred embodiment, the sample fluid is then directed to a rotatory injection valve 55 and then to a separation section of the instrument 20 where the ion chromatography process is accomplished. Although the current inventor has modified other portions of the instrument 20, for the purposes of this disclosure, the data generation and measurement processes can be conducted using known components and processes For the foregoing reasons, it is clear that the method and apparatus described herein provides an innovative portable ion chromatography sampling system. The current system may be modified in multiple ways and applied in various technological applications. The disclosed method and apparatus may be modified and customized as required by a specific operation or application, and the individual components may be modified and defined, as required, to achieve the desired result.

The terms "top", "bottom", upward and "downward" are used in this disclosure so that the embodiment(s) shown in the drawings are more easily understood and intuitive. However, these terms are not intended to limit the specification. In operation, the orientation of the described components may not correspond to the drawings.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

What is claimed is:

1. An auto-sampling system for a testing instrument, the system comprising:
   a watertight outer shell;
   a control unit enclosed within the shell;
   a syringe pump in communication with the control unit;
   a sample inlet filter in hydraulic communication with the syringe pump, the sample inlet filter comprising:
      (a) an unfiltered reservoir having an inlet and an outlet so that the unfiltered reservoir comprises a continuous flow reservoir;
      (b) a filtered reservoir smaller than the unfiltered reservoir; and,
      (c) a filter element positioned between the filtered reservoir and the unfiltered reservoir;
   a syringe pump having a plunger;
   an inline digester in hydraulic communication with the syringe pump and the sample inlet filter;
   a check valve positioned between the syringe pump and the sample inlet filter;
   wherein the system is structured so that, when directed by the control unit, the plunger of the syringe pump is retracted and suction force from the syringe pump causes a sample fluid to move from the unfiltered reservoir into the filtered reservoir, through the inline digester, and through the check valve; when further directed by the control unit, the plunger is advanced, so that the sample fluid is injected back through the check valve and into a testing portion of an instrument.

2. The system of claim 1 wherein the inline digester boils sample fluid as the sample fluid passes through the digester.

3. The system of claim 1 wherein the inline digester is positioned in series between the sample inlet filter and the syringe pump.

4. The system of claim 1 further comprising a three-port valve, wherein one of the ports is in communication with a reagent reservoir holding a reagent so that the reagent from the reagent reservoir is selectively injected into the sample fluid.

5. The system of claim 4 wherein the control unit is configured to cause selective injection of the reagent into the sample fluid after the sample fluid passes through the sample inlet filter.

6. The system of claim 5 wherein the control unit is configured to selectively inject the reagent into the sample fluid so that the reagent and the sample fluid are mixed at least partially in the in-line digester.

7. The system of claim 4 wherein the reagent comprises one or more persulfate reagents.

8. The system of claim 1 wherein a volumetric ratio of the filtered reservoir to the unfiltered reservoir is about 1 to 10.

9. The system of claim 1 wherein the filter element comprises a membrane disk.

10. The system of claim 9 wherein the membrane disk comprises a polyethersulfone membrane disk.

11. The system of claim 10 wherein the polyethersulfone membrane disk has a nominal pore size of about 0.45 μm.

12. The system of claim 1 wherein the filter element has a pore size in the range of 0.22 μm to 2.0 μm.

13. The system of claim 1 wherein the system is structured so that, in operation, the system is capable of, and configured to, operate one of floating on, or immersed in, the sample fluid.

14. A field-portable ion chromatography auto-sampling system, the system comprising:
 a sample inlet filter comprising:
  (a) an unfiltered reservoir having an inlet and an outlet so that the unfiltered reservoir comprises a continuous flow reservoir;
  (b) a filtered reservoir smaller than the unfiltered reservoir; and,
  (c) a filter element positioned between the filtered reservoir and the unfiltered reservoir;
 a syringe pump having a plunger; and,
 an inline digester, the inline digester being positioned in series between the sample inlet filter and the syringe pump;
 wherein the system is structured so that when the plunger of the syringe pump is retracted, suction force from the syringe pump causes a sample fluid to move from the unfiltered reservoir into the filtered reservoir through the inline digester, and into a sample loop between an inlet for the syringe pump and a check valve, and when the plunger is advanced, the system is structured so that the sample fluid is injected back through the check valve and into a testing portion of the chromatography auto-sampling system.

15. The system of claim 14 wherein the system is structured so that, in operation, the field-portable ion chromatography instrument is capable of and configured to operate one of floating on, or immersed in, the sample fluid.

16. The system of claim 14 wherein the check valve is positioned between the syringe pump and the sample inlet filter so that when the plunger is retracted, the sample fluid moves from the sample inlet filter through the check valve.

17. A method of drawing a sample fluid into a field-portable ion chromatography instrument, wherein the ion chromatography instrument is either floating or immersed in the sample fluid, the method comprising the steps of:
 (a) providing the field-portable ion chromatography instrument, which comprises:
  a sample inlet filter comprising:
   an unfiltered reservoir having an inlet and an outlet so that the unfiltered reservoir comprises a continuous flow reservoir;
   a filtered reservoir smaller than the unfiltered reservoir; and,
   a filter element positioned between the filtered reservoir and the unfiltered reservoir;
  a syringe pump having a plunger; and
  an inline digester, the inline digester being positioned in series between the sample inlet filter and the syringe pump;
 wherein the system is structured so that when the plunger of the syringe pump is retracted, suction force from the syringe pump causes a sample fluid to move from the unfiltered reservoir into the filtered reservoir through the inline digester, and into a sample loop between an inlet for the syringe pump and a check valve, and when the plunger is advanced, the instrument is structured so that the sample fluid is injected back through the check valve and into a testing portion of the field-portable ion chromatography instrument;
 (b) retracting the plunger of the syringe pump so that the sample fluid moves from the unfiltered reservoir into the filtered reservoir and into the sample loop; and then,
 (c) advancing the plunger so that the sample fluid is injected into the testing portion of the field-portable ion chromatography instrument.

* * * * *